US007618933B2

(12) United States Patent
Browning et al.

(10) Patent No.: US 7,618,933 B2
(45) Date of Patent: Nov. 17, 2009

(54) TREATMENT OF FOLLICULAR LYMPHOMAS USING INHIBITORS OF THE LT PATHWAY

(75) Inventors: Jeffrey L. Browning, Cambridge, MA (US); Jeanette Thorbecke, Douglaston, NY (US); Vincent Tsiagbe, New Rochelle, NY (US)

(73) Assignees: New York University, New York, NY (US); Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 11/411,049

(22) Filed: Apr. 25, 2006

(65) Prior Publication Data

US 2006/0280722 A1     Dec. 14, 2006

Related U.S. Application Data

(60) Division of application No. 09/626,219, filed on Jul. 26, 2000, now Pat. No. 7,060,667, which is a continuation-in-part of application No. PCT/US99/01928, filed on Jan. 29, 1999.

(60) Provisional application No. 60/073,112, filed on Jan. 30, 1998, provisional application No. 60/073,410, filed on Feb. 2, 1998.

(51) Int. Cl.
*A61K 38/00* (2006.01)
(52) U.S. Cl. .................................. 512/2; 424/134.1
(58) Field of Classification Search ................... None
See application file for complete search history.

(56) References Cited

U.S. PATENT DOCUMENTS

| 4,816,567 | A | 3/1989 | Cabilly et al. |
| 5,225,538 | A | 7/1993 | Capon et al. |
| 5,661,004 | A | 8/1997 | Browning et al. |
| 5,670,149 | A | 9/1997 | Browning et al. |
| 5,795,964 | A | 8/1998 | Browning et al. |
| 5,925,351 | A | 7/1999 | Browning et al. |
| 6,312,691 | B1 | 11/2001 | Browning et al. |
| 6,403,087 | B1 | 6/2002 | Browning et al. |
| 6,669,941 | B1 | 12/2003 | Browning et al. |
| 7,001,598 | B2 | 2/2006 | Browning et al. |
| 7,030,080 | B2 | 4/2006 | Browning et al. |
| 7,060,667 | B1 | 6/2006 | Browning et al. |
| 7,255,854 | B1 | 8/2007 | Browning et al. |
| 7,309,492 | B2 | 12/2007 | Browning et al. |
| 2002/0039580 | A1 | 4/2002 | Browning et al. |
| 2004/0198635 | A1 | 10/2004 | Browning et al. |
| 2005/0037003 | A1 | 2/2005 | Browning et al. |
| 2005/0281811 | A1 | 12/2005 | Browning et al. |

FOREIGN PATENT DOCUMENTS

| EP | 0873998 A2 | 10/1998 |
| WO | WO-92/00329 A1 | 1/1992 |
| WO | WO-94/04679 A1 | 3/1994 |
| WO | WO-94/13808 A2 | 6/1994 |
| WO | WO-96/01121 A1 | 1/1996 |
| WO | WO-96/23071 A2 | 8/1996 |
| WO | WO-97/03687 A1 | 2/1997 |

OTHER PUBLICATIONS

Alexopoulou, Lena et al., "Immunoregulatory Activities of Transmembrane TNF Revealed in Transgenic and Mutant Mice," *6th International TNF Congress*, p. 228, Poster Presentation No. 110 (1996).
Androlewicz, Matthew J. et al., "Lymphotoxin Is Expressed as a Heteromeric Complex with a Distinct 33-kDa Glycoprotein on the Surface of an Activated Human T Cell Hybridoma," *The Journal of Biological Chemistry*, vol. 267(4):2542-2547 (1992).
Arulanandam, Antonio R.N. et al., "A Soluble Multimeric Recombinant CD2 Protein Identifies CD48 as a Low Affinity Ligand for Human CD2: Divergence of CD2 Ligands during the Evolution of Humans and Mice," *J. Exp. Med.*, vol. 177:1439-1450 (1993).
Banks, Theresa A. et al., "Lymphotoxin-α-Deficient Mice, Effects on Secondary Lymphoid Organ Development and Humoral Immune Responsiveness," *The Journal of Immunology*, vol. 155:1685-1693 (1995).
Browning, Jeffrey L. et al., "Characterization of Surface Symphotoxin Forms, Use of Specific Monoclonal Antibodies and Soluble Receptors," *The Journal of Immunology*, vol. 154:33-46 (1995).
Browning, Jeffrey L. et al., "Lymphotoxin and an Associated 33-kDa Glycoprotein are Expressed on the Surface of an Activated Human T Cell Hybridoma," *The Journal of Immunology*, vol. 147:1230-1237 (1991).
Browning, Jeffrey L. et al., "Lymphotoxin β, a Novel Member of the TNF Family That Forms a Heteromeric Complex with Lymphotoxin on the Cell Surface," *Cell*, vol. 72:847-856 (1993).
Browning, Jeffrey L. et al., "Signaling through the Lymphotoxin β Receptor Induces the Death of Some Adenocarcinoma Tumor Lines," *J. Exp. Med.*, vol. 183:867-878 (1996).
Crowe, Paul D. et al., "A Lymphotoxin-β-Specific Receptor," *Science*, vol. 264:707-710 (1994).
De Togni et al. "Abnormal Development of Peripheral Lympoid Organs in Mice Deficient in Lymphotoxin" *Science* 264:703-708 (1994).
Erickson, Sharon L. et al., "Decreased sensitivity to tumour-necrosis factor but normal T-cell development in TNF receptor-2-deficient mice," *Nature*, vol. 372:560-563 (1994).
Ettinger, Rachel et al., "Disrupted splenic architecture, but normal lymph node development in mice expressing a soluble lymphotoxin-β receptor-IgG1 fusion protein," *Proc. Natl. Acad. Sci. USA*, vol. 93:13102-13107 (1996).
Hagemeijer, A., "Cytogenetics and oncogenes," *Leukemia*, vol. 6(Suppl. 4):16-18 (1992).
Higuchi, Masahiro et al., "Inhibition of Ligand Binding and Antiproliferative Effects of Tumor Necrosis Factor and Lymphotoxin by Soluble Forms of Recombinant P60 and P80 Receptors," *Biochemical and Biophysical Research Communications*, vol. 182(2):638-643 (1992).
Hillion et al. (1993) *Leukemia* 7(3):410-7.

(Continued)

*Primary Examiner*—Misook Yu
(74) *Attorney, Agent, or Firm*—Lahive & Cockfield, LLP; Amy E. Mandragouras, Esq.; Megan E. Williams

(57) ABSTRACT

Therapeutic uses of inhibitors of the Lymphotoxin Pathway to treat tumors, specifically to treat follicular lymphomas.

20 Claims, No Drawings

OTHER PUBLICATIONS

Katz, Irene R. et al., "Growth of SJL / J-Derived Transplantable Reticulum Cell Sarcoma Related to Its Ability to Induce T-Cell Proliferation in the Host," *Cellular Immunology*, vol. 65:84-92 (1981).

Lane, Peter et al., "Activated human T cells express a ligand for the human B cell-associated antigen CD40 which participates in T cell-dependent activation of B lymphocytes," *Eur. J. Immunol.*, vol. 22:2573-2578 (1992).

Lasky, J.L. et al., "Characterization and Growth Factor Requirements of SJL Lymphomas, I. Development of a B Cell Growth Factor-Dependent in Vitro Cells Line, cRCS-X," *The Journal of Immunology*, vol. 14:679-687 (1988).

Lasky, Jennifer L. et al., "Characterization and growth factor requirements of SJL lymphomas, II. Interleukin 5 dependence of the in vitro cell line, cRCS-X, and influence of other cytokines," *Eur. J. Immunol.*, vol. 19:365-371 (1989).

Le Hir, Michel et al., "Differentiation of Follicular Dendritic Cells and Full Antibody Responses Require Tumor Necrosis Factor Receptor-1 Signaling," *J. Exp. Med.*, vol. 183:2367-2372 (1996).

Mackay, Fabienne et al., "Lymphotoxin but not tumor necrosis factor functions to maintain splenic architecture and humoral responsiveness in adult mice," *Eur. J. Immunol.*, vol. 27: 2033-2042 (1997).

Matsumoto, Mitsuru et al., "Affinity maturation without germinal centres in lymphotoxin-α-deficient mice," *Nature*, vol. 382:462-466 (1996).

Matsumoto, Mitsuru et al., "Distinct Roles of Lymphotoxin α and the Type I Tumor Necrosis Factor (TNF) Receptor in the Establishment of Follicular Dendritic Cells from Non-Bone Marrow-derived Cells," *J. Exp. Med.*, vol. 186(12):1997-2004 (1997).

Matsumoto, Mitsuru et al., "Role of Lymphotoxin and the Type I TNF Receptor in the Formation of Germinal Centers," *Science*, vol. 271:1289-1291 (1996).

Morrison, Sherie L. et al., "Chimerica human antibody molecules: Mouse antigen-binding domains with human constant region domains," *Proc. Natl. Acad. Sci. USA*, vol. 81:6851-6855 (1984).

Morrison, Sherie L., "In Vitro Antibodies: Strategies for Production and Application," *Annu. Rev. Immunol.*, vol. 10:239-265 (1992).

Pasparakis, Manolis et al., "Immune and Inflammatory Responses in the TNFα Deficient Mice: A Critical Requirement for TNFα in Germinal Centre Formation and in the Maturation of the Humoral Immune Response," *Eur. Cytokine Netw.*, vol. 7(2):239, Poster Session No. 132 (1996).

Pfeffer, Klaus et al., "Mice Deficient for the 55 kd Tumor Necrosis Factor Receptor Are Resistant to Endotoxic Shock, yet Succumb to *L. monocytogenes* Infection," *Cell*, vol. 73:457-467 (1993).

Picarella, Dominic E. et al., "Insulitis in transgenic mice expressing tumor necrosis factor β (lymphotoxin) in the pancreas," *Proc. Natl. Acad. Sci. USA*, vol. 89:10036-10040 (1992).

Picker, Louis J. et al., "Physiological and Molecular Mechanisms of Lymphocyte Homing," *Annu. Rev. Immunol.*, vol. 10:561-591 (1992).

Ponzio, Nicholas M. et al., "Host-Tumor Interactions in the SJL Lymphoma Model," *Intern. Rev. Immunol.*, vol. 1:273-301 (1986).

Qin, Zhihai et al., "Human Lymphotoxin Has at Least Equal Antitumor Activity in Comparison to Human Tumor Necrosis Factor But Is Less Toxic in Mice," *Blood*, vol. 85(10):2779-2785 (1995).

Queen, Cary et al., "A humanized antibody that binds to the interleukin 2 receptor," *Proc. Natl. Acad. Sci. USA*, vol. 86:10029-10033 (1989).

Reisfeld, Ralph A. et al., "Involvement of B Lymphocytes in the Growth Inhibition of Human Pulmonary Melanoma Metastases in Athymic *nu/nu* Mice by an Antibody-Lymphotoxin Fusion Protein," *Cancer Research*, vol. 56:1707-1712 (1996).

Rennert, P.D. et al., "Normal Development of Lymph Nodes is Disrupted by Soluble LT beta Receptor—Ig Fusion Protein," *European Cytokine Network*, vol. 7(2):167, No. 17 (1996).

Rennert, Paul D. et al., "Surface Lymphotoxin α/β Complex Is Required for the Development of Peripheral Lymphoid Organs," *J. Exp. Med.*, vol. 184:1999-2006 (1996).

Robert et al. "Turning off follicular dendritic cells" *Nature* 395:26 (1998).

Rothe, Joachim et al., "Mice lacking the tumor necrosis factor receptor 1 are resistant to TNF-mediated toxicity but highly susceptible to infection by *Listeria monocytogenes*," *Nature*, vol. 364:798-802 (1993).

Selmaj, Krzysztof et al., "Identification of Lymphotoxin and Tumor Necrosis Factor in Multiple Sclerosis Lesions," *J. Clin. Invest.*, vol. 87:949-954 (1991).

Traunecker, André et al., "Highly efficient neutralization of HIV with recombinant CD4-immunoglobulin molecules," *Nature*, vol. 339:68-70 (1989).

Tsiagbe, V.K. et al., "Syngeneic Response to SJL Follicular Center B Cell Lymphoma (Reticular Cell Sarcoma) Cells Is Primarily in Vβ16+ CD4+ T Cells," *The Journal of Immunology*, vol. 150(12):5519-5528 (1993).

Tsiagbe, V.K. et al., "The Physiology of Germinal Centers," *Critical Reviews in Immunology*, vol. 16:381-421 (1996).

Ware, C.F. et al., "The Ligands and Receptors of the Lymphotoxin System," *Current Topics Microbiol. Immunol.*, vol. 198:175-218 (1995).

Winter et al. "Man-made antibodies" *Nature* 349:293-299 (1991).

Wong, G.H.W. et al., "Strategies for Manipulating Apoptosis for Cancer Therapy With Tumor Necrosis Factor and Lymphotoxin," *Journal of Cellular Biochemistry*, vol. 60:56-60 (1996).

Mackay, Fabienne et al., "Turning off follicular dendritic cells," *Nature*, vol. 395:26-27 (1998).

Séité, Paule et al., "BCL2 Gene Activation and Protein Expression in Follicular Lymphoma: a Report on 64 Cases," *Leukemia*, vol. 7(3):410-417 (1993).

SEQUENCE LISTING

```
<160> NUMBER OF SEQ ID NOS: 1

<210> SEQ ID NO 1
<211> LENGTH: 197
<212> TYPE: PRT
<213> ORGANISM: Mouse

<400> SEQUENCE: 1

Ser Gln Pro Gln Ala Val Pro Pro Tyr Ala Ser Glu Asn Gln Thr Cys
1               5                   10                  15

Arg Asp Gln Glu Lys Glu Tyr Tyr Glu Pro Gln His Arg Ile Cys Cys
                20                  25                  30

Ser Arg Cys Pro Pro Gly Thr Tyr Val Ser Ala Lys Cys Ser Arg Ile
            35                  40                  45

Arg Asp Thr Val CYs Ala Thr Cys Ala Glu Asn Ser Tyr Asn Glu His
            50              55                  60

Trp Asn Tyr Leu Thr Ile Cys Gln Leu Cys Arg Pro Cys Asp Pro Val
65                  70                  75                  80

Met Gly Leu Glu Glu Ile Ala Pro Cys Thr Ser Lys Arg Lys Thr Gln
                85                  90                  95

Cys Arg Cys Gln Pro Gly Met Phe Cys Ala Ala Trp Ala Leu Glu Cys
                100                 105                 110

Thr His Cys Glu Leu Leu Ser Asp Cys Pro Pro Gly Thr Glu Ala Glu
            115                 120                 125

Leu Lys Asp Glu Val Gly Lys Gly Asn Asn His Cys Val Pro Cys Lys
        130                 135                 140

Ala Gly His Phe Gln Asn Thr Ser Ser Pro Ser Ala Arg Cys Gln Pro
145                 150                 155                 160

His Thr Arg Cys Glu Asn Gln Gly Leu Val Glu Ala Ala Pro Gly Thr
                165                 170                 175

Ala Gln Ser Asp Thr Thr Cys Lys Asn Pro Leu Gln Pro Leu Pro Pro
            180                 185                 190

Glu Met Ser Gly Thr
            195
```

TREATMENT OF FOLLICULAR LYMPHOMAS USING INHIBITORS OF THE LT PATHWAY

RELATED APPLICATIONS

This is a divisional of U.S. patent application Ser. No. 09/626,219, filed on Jul. 26, 2000 as a continuation-in-part of PCT/US99/01928, which was filed on Jan. 29, 1999 and claims priority to U.S. Patent Application No. 60/073,112, filed Jan. 30, 1998 and U.S. Patent Application No. 60/073,410, filed Feb. 2, 1998. The entire disclosure of each of the aforesaid patent applications are incorporated herein by reference.

FIELD OF THE INVENTION

The present invention relates to compositions, and therapeutic uses of inhibitors of the Lymphotoxin pathway to treat tumors, specifically to treat lymphomas derived from germinal centers (follicular lymphomas).

BACKGROUND OF THE INVENTION

The tumor-necrosis factor (TNF)-related cytokines are mediators of host defense and immune regulation. Members of this family exist in membrane-anchored forms, acting locally through cell-to-cell contact, or as secreted proteins capable of diffusing to more distant targets. A parallel family of receptors signals the presence of these molecules leading to the initiation of cell death or cellular proliferation and differentiation in the target tissue. Presently, the TNF family of ligands and receptors has at least 11 recognized receptor-ligand pairs, including: TNF:TNF-R; LT-α:TNF-R; LT-α/β: LT-β-R; FasL:Fas; CD40L:CD40; CD30L:CD30; CD27L: CD27; OX40L:OX40 and 4-1BBL:4-1BB.

TNF family members can best be described as master switches in the immune system controlling both cell survival and differentiation. Only TNF and LT-α are currently recognized as secreted cytokines contrasting with the other predominantly membrane-anchored members of the TNF family. While a membrane form of TNF has been well characterized and is likely to have unique biological roles, secreted TNF functions as a general alarm signaling to cells more distant from the site of the triggering event. Thus TNF secretion can amplify an event leading to the well-described changes in the vasculature lining and the inflammatory state of cells. In contrast, the membrane bound members of the family send signals though the TNF type receptors only to cells in direct contact. For example T cells provide CD40 mediated Similar cell-cell contact limitations on the ability to induce cell death apply to the well-studied Fas system.

Most membrane-associated LT-α/β complexes ("surface LT") have a LT-α1/β2 stoichiometry. (Browning et al., Cell, 72, pp. 847-56 (1993); Browning et al., J. Immunol., 154, pp. 33-46 (1995)). Surface LT ligands do not bind TNF-R with high affinity and do not activate TNF-R signaling. The LT-β receptor (LT-β-R), does however bind these surface lymphotoxin complexes with high affinity (Crowe et al., Science, 264, pp. 707-10 (1994)).

LTβ-R signaling, like TNF-R signaling, has anti-proliferative effects and can be cytotoxic to tumor cells. In applicants' co-pending U.S. application Ser. No. 08/378,968, compositions and methods for selectively stimulating LT-β-R using LT-β-R activating agents are disclosed. LT-β-R activating agents are useful for inhibiting tumor cell growth without co-activating TNF-R-induced proinflammatory or immunoregulatory pathways.

Recent gene targeting studies suggest a role for LT-α/β in the development of secondary lymphoid organs. (Banks et al., J. Immunol., 155, pp. 1685-1693 (1995); De Togni et al., Science, 264, pp. 703-706 (1994)). Indeed, LT-α-deficient mice lack lymph nodes (LN) and Peyer's patches (PP). Moreover, their spleens have disrupted architecture and the expression of functional markers on cells of the splenic marginal zone is altered. (Banks et al., 1995; De Togni et al., Science, 264, pp. 703-706 (1994), Matsumoto et al., Science, 271, pp. 1289-1291 (1996)). None of these characteristics have been described for either of the TNF receptor knock out mice. (Erickson et al., Nature, 372, pp. 560-563 (1994); Pfeffer et al., Cell, 73, pp. 457-467 (1993); Rothe et al., Nature, 364, pp. 798-802 (1993). Applicants have recently defined a role for membrane LT-α/β complexes in secondary lymphoid organ development by showing that the progeny of mice which had been injected during gestation with a soluble form of mouse LT-β-R fused to the human IgG1 Fc portion (LT-β-R-Ig) lacked most lymph nodes and showed disrupted splenic architecture. (Rennert et al, 1996, "Surface Lymphotoxin alpha/beta complex is required for the development of peripheral lymphoid organs." J. Exp Med, 184: 1999-2006). In another study, mice transgenic for a similar LT-β-R-Ig construct which starts to be expressed three days after birth, were shown to have LN. However, their splenic architecture was disrupted and several markers of splenic marginal zone cells were not expressed (Ettinger et al., "Disrupted splenic architecture, but normal lymph node development in mice expressing a soluble LTβ-R/IgG1 fusion protein"., Proc. Natl. Acad. Sci. U.S.A. 93: 13102-7). Together these data indicate there is a temporal requirement for membrane LT functions to mediate effects on the development of secondary lymphoid organs, but not for effects on splenic architecture.

The TNF system may also function in development of the spleen. Splenic marginal zone cells of TNF-deficient mice do not express macrophage markers or MAdCAM-1 (Alexopoulou et al., 60th Int. TNF Congress, Eur. Cytokine Network, pp. 228 (1996); Pasparakis et al., 60th Int. TNF Congress, Eur. Cytokine Network, pp. 239 (1996)). TNF-R55-deficient mice also lack MAdCAM-1 (but not MOMA-1) staining in the splenic marginal zone. (Neumann et al., J. Exp. Med., 184, pp. 259-264 (1996), Matsumoto et al., Science, 271, pp. 1289-1291 (1996)). The expression of these markers as seen in the spleen of TNF-R75-deficient mice appears normal. (Matsumoto et al., Science, 271, pp. 1289-1291 (1996)).

Lymphoid-like tissues do not only arise as a part of developmental processes but also appear under some pathological circumstances such as chronic inflammation, a process recently termed neolymphoorganogenesis. (Picker and Butcher, Annu. Rev. Immunol., 10, pp. 561-591 (1992), Kratz, et al., J. Exp. Med., 183, pp. 1461-1471 (1996)). TNF family members apparently influence such processes. Mice transgenic for the LT-α gene driven by the rat insulin promoter (RIP-LT) developed LT-induced chronic inflammatory lesions with characteristics of organized lymphoid tissues. (Kratz, et al., J. Exp. Med., 1183, pp. 1461-1471 (1996); Picarella et al., Proc. Natl. Acad. Sci., 89, pp. 10036-10040 (1992)).

The evaluation of LT function during a T cell-dependent immune response, using LT-α-deficient mice, showed the necessity of LT for GC formation, possibly for maintaining an organized follicular dendritic cell (FDCs) structure, and for humoral responses. (Banks et al., J. Immunol., 155, pp. 1685-1693 (1995); Matsumoto et al., Science, 271, pp. 1289-1291 (1996); Matsumoto et al., Nature, 382, pp. 462-466 (1996)). TNF-R55-deficient mice also lack FDCs, fail to develop GC and fail to develop an optimal antibody response to sheep red blood cells (SRBC). This suggests that TNF-R55 might be triggered by soluble LT or TNF signals for most of these responses (Le Hir et al., *J. Exp. Med.*, 183, pp. 2367-2372 (1996), Alexopoulou et al., *60th Int. TNF Congress. Eur. Cytokine Network*, pp. 228 (1996); Pasparakis et al., *60th Int. TNF Congress, Eur. Cytokine Network*, pp. 239 (1996)).

The LT-β-receptor, a member of the TNF family of receptors, specifically binds to surface LT ligands. LT-β-R binds LT heteromeric complexes (predominantly LT-α1/β2 and LT-α2/β1) but does not bind TNF or LT-α(Crowe et al., *Science*, 264, pp. 707-10 (1994)). LT-β-R mRNAs are found in the human spleen, thymus and in general organs with immune system involvement. Although studies on LT-β-R expression are in their early stages, LT-β-R expression patterns appear to be similar to those reported for TNF-R55 except that LT-β-R is lacking on peripheral blood T and B cells and T and B cell lines.

Cell surface lymphotoxin (LT) complexes have been characterized in $CD4^+$ T cell hybridoma cells (II-23.D7) which express high levels of LT. (Browning et al., *J. Immunol.*, 147, pp. 1230-37 (1991); Androlewicz et al., *J. Biol. Chem.*, 267, pp. 2542-47 (1992), both of which are herein incorporated by reference). The expression and biological roles of LTβ-R, LT subunits and surface LT complexes have been reviewed by C. F. Ware et al. "The ligands and receptors of the lymphotoxin system", in *Pathways for Cytolysis, Current Topics Microbiol. Immunol.*, Springer-Verlag, pp. 175-218 (1995) specifically incorporated by reference herein.

LT-α expression is induced and LT-α secreted primarily by activated T and B lymphocytes and natural killer (NK) cells. Among the T helper cells, LT-α appears to be produced by Th1 but not Th2 cells. LT-α has also been detected in melanocytes. Microglia and T cells in lesions of multiple sclerosis patients can also be stained with anti-LT-α antisera (Selmaj et al., *J. Clin. Invest.*, 87, pp. 949-954 (1991)).

Lymphotoxin β (also called p33) is expressed on the surface of human and mouse T lymphocytes, T cell lines, B cell lines and lymphokine-activated killer (LAK) cells. LTβ is the subject of applicants' co-pending international applications PCT/US91/04588, published Jan. 9, 1992 as WO 92/00329; and PCT/US93/11669, published Jun. 23, 1994 as WO 94/13808, which are herein incorporated by reference.

Surface LT complexes are primarily expressed by activated T (helper, Th1, and killer cells) and B lymphocytes and natural killer (NK) cells as defined by FACS analysis or immunohistology using anti-LT antibodies or soluble LT-β-R-Ig fusion proteins. In applicants copending U.S. application Ser. No. 08/505,606, filed Jul. 21, 1995, compositions and methods for using soluble LT-β receptors and anti-LT-β receptor and ligand specific antibodies as therapeutics for the treatment of immunological diseases mediated by Th1 cells are disclosed. Surface LT has also been described on human cytotoxic T lymphocyte (CTL) clones, activated peripheral mononuclear lymphocytes (PML), IL-2-activated peripheral blood lymphocytes (LAK cells), pokeweed mitogen-activated or anti-CD40-activated peripheral B lymphocytes (PBL) and various lymphoid tumors of T and B cell lineage. Engagement of alloantigen-bearing target cells specifically induces surface LT expression by $CD8^+$ and $CD4^+$ CTL clones.

Applicants have described herein several immunological functions for surface LT, and show the effects of LT-α/β binding reagents on the generation and character of immunoglobulin responses, maintenance of the cellular organization of secondary lymphoid tissues including effects on the differentiation state of follicular dendritic cells and germinal center formation, and addressing expression levels which influence cell trafficking. Thus applicants define therapeutic applications for surface LT-α/β and LT-α receptor binding agents.

Studies have shown that B cells are activated in the lymph nodes (LN) and spleen following encounters with various antigens. In a specialized structure called a germinal center which forms in the B cell rich regions of LN and spleen, the B cells mature and memory B cells form (Tsiagbe, et al. *Crit. Rev. Immunol.* 16, 381-421 (1996)). B cells are capable of undergoing transformation into tumors at most points during their development (Freedman, et al, *Cancer Medicine* $3^{rd\,Ed}$., pp. 2028-2068 (1994)). Transformation of B cells leads to lymphomas and those derived from B cells in germinal centers are often called follicular lymphomas. The exact delineation of the various subsets of lymphomas is still in transition as more surface markers are found permitting a more precise designation of the cell of origin. Follicular lymphomas can be divided into a number of subgroups based on the stage or type of B cell that is proliferating and the prognosis varies depending on the cell type. Conventional chemotherapy regimes are capable of affecting a cure in many of the patients with low-grade type cells. Nonetheless a portion of these patients are resistant to chemotherapy and have a poor prognosis.

Therefore, despite the progress in treating tumors, there remains a need for a treatment for those tumors especially for those follicular lymphomas typically resistant to chemotherapy, as well as for treatment regimes with fewer side effects than existing therapies.

SUMMARY OF THE INVENTION

The present invention provides methods and compositions for the treatment of tumors such as follicular lymphomas which overcome certain problems existing with present therapies, and offers an alternative therapy for those with tumors resistant to traditional chemotherapy.

In certain embodiments, the claimed invention relates to methods of treating a subject having a follicular lymphoma comprising administering to the subject an effective amount of a composition which blocks the interaction of the LT-α/β heteromer with its receptor. Preferred compositions in various embodiments include, but are not limited to, soluble lymphotoxin-βreceptors, antibodies directed against the LT-β receptor, and antibodies directed against surface LT ligand. More preferred are soluble lymphotoxin-β receptors having a ligand binding domain that can selectively bind to a surface LT ligand, such as, for example, a soluble LT-β-R form fused to a human immunoglobulin Fc domain. Additionally, preferred compositions include monoclonal antibodies which are directed against the LT-β receptor, including antibodies which are humanized, chimeric or otherwise altered.

In other embodiments of the invention, the claims encompass methods of treatment of subjects having follicular tumors wherein the blocking agents are administered until regression or arrest of tumor growth is noted. In certain embodiments, the LT pathway blocking agents are administered in combination with other agents known to be useful in treating tumors, such as, for example chemotherapy regimens. Additionally, the methods of the invention may in certain embodiments further comprise treating the subject with radiation or bone marrow transplantation.

In yet other embodiments, the claimed methods comprise the administration of LT-β-R blocking agents in conjunction with blocking agents of pathways of other members of the TNF family. For example, TNF blocking agents may be administered in conjunction with, simultaneously or concomitantly, a blocking agent of the claimed invention.

DETAILED DESCRIPTION OF THE INVENTION

The present invention provides methods and compositions for the treatment of tumors, such as follicular tumors, specifically follicular lymphomas.

The terms "immunoglobulin response" or "humoral response" as used herein refer to the immunological response of an animal to a foreign antigen whereby the animal produces antibodies to the foreign antigen. The Th2 class of T helper cells are important to the efficient production of high affinity antibodies.

The term "germinal center" as used herein refers to a secondary B cell follicle which forms after antigen immunization. The appearance of this histologic site correlates with optimal memory generation, isotype switching, somatic hypermutation and thus the affinity maturation of an antibody response.

The terms "marginal zone" or "marginal-zone type area" refer to histologically described compartments of the secondary lymphoid tissues comprised primarily of marginal zone macrophages (MZM), metallophilic macrophages (MM), marginal zone B cells and reticular cells, and also T cells and dendritic cells. The arterial blood stream opens into the marginal sinuses thus giving antigens direct access to these cells and promoting cellular reactions to antigens at this site.

The term "T helper (Th) cells" as used herein, refers to a functional subclass of T cells which help to generate cytotoxic T cells and which cooperate with B cells to stimulate antibody production. Helper T cells recognize antigen in association with class II MHC molecules and provide contact dependent and contact independent (cytokine) signals to effector cells.

The term "Fc domain" of an antibody refers to a part of the molecule comprising the hinge, CH2 and CH3 domains, but lacking the antigen binding sites. The term is also meant to include the equivalent regions of an IgM or other antibody isotype.

The term "anti-LT-$\beta$ receptor antibody" refers to any antibody that specifically binds to at least one epitope of the LT-$\beta$ receptor.

The term "anti-LT antibody" refers to any antibody that specifically binds to at least one epitope of LT-$\alpha$, LT-$\beta$ or a LT-$\alpha$/$\beta$ complex.

The term "LT-$\beta$-R signaling" refers to molecular reactions associated with the LT-$\beta$-R pathway and subsequent molecular reactions which result therefrom.

The term "LT-$\beta$-R blocking agent" refers to an agent that can diminish ligand binding to LT-$\beta$-R, cell surface L-$\beta$-R clustering or LT-$\beta$-R signaling, or that can influence how the LT-$\beta$-R signal is interpreted within the cell.

An LT-$\beta$-R blocking agent that acts at the step of ligand-receptor binding can inhibit LT ligand binding to the LT-$\beta$-R by at least 20%. Examples of LT-$\beta$-R blocking agents include soluble LT-$\beta$-R-Fc molecules, and anti-LT-$\alpha$, anti-LT-$\beta$, anti-LT-$\alpha$/$\beta$ and anti-LT-$\beta$-R Abs. Preferably, the antibodies do not cross-react with the secreted form of LT-$\alpha$.

The term "LT-$\beta$-R biological activity" refers to: 1) the ability of the LT-$\beta$-R molecule or derivative to compete for soluble or surface LT ligand binding with soluble or surface LT-$\beta$-R molecules; or 2) native LT activity such as the ability to stimulate an immune regulatory response or cytotoxic activity.

The term "LT ligand" refers to an LT-$\alpha$/$\beta$ heteromeric complex or derivative thereof that can specifically bind to the LT$\beta$ receptor.

The term "LT-$\beta$-R ligand binding domain" refers to the portion or portions of the LT-R that are involved in specific recognition of and interaction with a LT ligand.

The terms "surface LT" and "surface LT complex" refer to a complex comprising LT-$\alpha$ and membrane-bound LT-$\beta$ subunits—including mutant, altered and chimeric forms of one or more of the subunits—which is displayed on the cell surface. "Surface LT ligand" refers to a surface LT complex or derivative thereof that can specifically bind to the LT-$\beta$ receptor.

The term "subject" refers to an animal, or to one or more cells derived from an animal. Preferably, the animal is a mammal. Cells may be in any form, including but not limited to cells retained in tissue, cell clusters, immortalized, transfected or transformed cells, and cells derived from an animal that has been physically or phenotypically altered.

As discussed above, transformation of B cells leads to lymphomas, and the transformation of B cells derived from germinal centers, the specialized structures found in the B cell rich regions of lymph nodes and the spleen, are referred to as follicular lymphomas. The germinal center B cell requires a specific environment to mature and proliferate and follicular dendritic cells provide both antigen and mostly likely specific signals for the germinal center B cells that trigger maturation, survival and proliferation. Studies in SJL mice which spontaneously form reticular cell sarcomas (RCS, an early designation of these types of tumors) have led to transplantable as well as in vitro cell lines of RCS(CRCS) that serve as a model for the interactions between the host and the tumor (Lasky, et al., *J. Immunol.*, 140, pp. 679-687, (1988) and Lasky, et al, *Eur. J. Immunol.*, 19, pp. 365-371, (1989). These RCS arise frequently in the LN of SJL mice and are heterogeneous containing a variety of hematopoietic cells. Considerable evidence indicates that these lymphomas are germinal center derived and require various signals or factors provided by the host to survive and proliferate (Ponzio, et al., *Intern. Rev. Immunol*, 1, pp. 365-371, (1986) and Tsiagbe et al, *J. Immunol.*, 150, pp. 5519-5528, (1993)). The ability to manipulate these survival signals provides a means of controlling the growth of these tumors One cell type called the follicular dendritic cell (FDC) is believed to be of paramount importance in the formation and function of the germinal center. Many different factors have been implicated in the survival and maintenance of germinal center B cells. Notably, members of the TNF family of cytokines are surface signaling ligands are involved both from the B cell side, e.g. CD40, and on the FDC side, e.g. TNF and lymphotoxin (LT) receptors. Mice deficient for either the LT or TNF axis have defects in the FDC and hence lack germinal centers (Matsumoto et al., *J. Exp. Med.*, 186, pp. 1997-2004, (1997)). The TNF axis is believed to be critical for the development of FDC although downstream roles probably exist. The LT axis appears to be more critical for the maintenance of FDC in a functional state. The LT system involves the signaling from various ligand positive lymphocytes to receptor positive cells that are most likely of a non-bone marrow derivation, i.e. possibly FDC derived, to maintain the FDC in their fully functional mature state. Applicants have found that blocking this pathway, with, for example, either antibodies to the LT ligands or a soluble receptor-immunoglobulin fusion protein, leads to a loss of mature FDC (Mackay and Browning, 1998 Nature, V. 395, pp 26-27, "Turning Off Follicular Dendritic Cells"). Furthermore, LT pathway inhibition leads to the loss of germinal center formation and some disorganization of the spleen (Mackay, et al., *Eur. J. Immunol.*, 27, pp. 2033-2042, (1997)).

Applicants for the first time describe herein that LT pathway inhibitors can disrupt the interactions between a follicular B cell lymphoma and its environment, i.e. the FDC, and lead to slowed or arrested growth of tumors. Hence, such inhibitors are useful in the management of intractable lymphomas or as a primary therapy, or in addition to conventional chemotherapy regimes. Specifically, although it has been suggested in the art that activation of the LT pathway could be implicated in tumor therapies, applicants have surprisingly discovered that the transient blocking of the LT pathway can lead to slowing or arrest of the growth of tumors, including for example, follicular lymphomas.

In its broader embodiments the present invention encompasses methods of treating subjects having tumors or lymphomas, specifically, follicular lymphomas, by administering an effective amount of a composition that inhibits the LT pathway. Specific inhibiting compositions may comprise soluble LT-β receptor, fusion proteins comprising LT-β-R, antibodies to LT-β-R, and antibodies to LT ligand. Such inhibiting compositions preferably include a pharmaceutically acceptable carrier. The subject in preferred applications is a mammal, most preferably, humans.

The methods of the invention comprise administering the compositions of the invention to the subject until some tumor regression, or arrest, is noted. The time of treatment may vary widely, and treatment may continue over the course of several weeks, to several months, or in some cases even longer. One skilled in the art is capable of determining when tumor regression or arrest has occurred, and any of the known methods can be used. The use of FACS markers to subdivide B lymphomas has improved considerably, and it may be expected that lymphomas of certain subtypes will prove to be most tractable to this type of therapy.

It is also likely that other immune system regulatory molecules such as other TNF family members may be involved in maintaining the immune organ architecture and therefore contribute to providing a favorable environment for lymphoma proliferation.

Therefore, combined inhibition of the LT and other pathways may be an effective treatment for certain subjects. For example, one may use inhibitors of the LT pathway in combination with, for example, blockers of the CD40/CD40 ligand pathway. Any composition which blocks the desired pathway can be used, such as, for example, antibodies, soluble ligands or receptors. It may be preferable to administer antibodies against CD40 Ligand in combination with inhibitors of the LT pathway. When administering more than one blocker of a TNF member pathway, the compositions may be administered substantially simultaneously, or alternatively, one blocker may be administered sequential to the other. One skilled in the art can easily determine the most effective treatment for a particular subject based upon the particular tumor being treated, and the condition of the subject.

Conventional chemotherapeutic protocols may be used to eliminate remaining tumor burden subsequent to treatment with the compositions of the invention, or in some cases, may be used simultaneously with, or prior to the compositions of the invention. LT pathway inhibitors may be used to arrest lymphoma growth prior to embarking on a conventional chemotherapy regime. It is likely that loss of growth/survival promoting signals may render a lymphoma more susceptible to chemotherapeutic agents, and therefore, it is preferred to administer the LT pathway inhibitor prior to administration of traditional chemotherapeutic agents.

EXAMPLE 1

Treatment of the SJL RCS Tumors with LT Pathway Inhibitor Reduces Total LN/Tumor Size SJL mice were treated either 3 days prior to the tumor transplantation (D-3), at the time of transplantation (D0), or 3 days post transplantation (D3) with 0.3-0.4 mg of mouse LTBR-hIgG1 fusion protein via the intraperitoneal route. Tumor transplantation was performed essentially as described (Katz, et al., *Cellular Immunol.*, 65, pp. 84-92, (1981)). 5×10$^6$ T cell depleted RCS cells were injected iv and allowed to seed the organs and grow. After 5-7 days, the mesenteric, brachial and axillary LN were dissected and their weight as a percentage of total body weight was calculated. Table I shows that LN size was reduced in all experiments. Spleen size was also reduced in 1 out of 3 experiments, but the reduction in spleen weight was not impressive. The reductions in LN weight ranged from about 50% with a single treatment to 80-90% with multiple dosing.

TABLE I

Inhibitory Effect of LTBR-Ig on RCS Growth in Normal SJL Mice.

| Mice Injected with (Day: Dose mg) | LN Wt$^a$ (n) | p | Spleen Wt.$^a$ (n) | p |
|---|---|---|---|---|
| Experiment 1 | | | | |
| huIgG control (Killed D5) | 2.70 +/− 0.37 (7) | | 3.18 +/− 0.37 (7) | |
| mLTβR-Ig$^c$ (D0, +3: 0.4, 0.3) | 1.42 +/− 0.15 (4) | <0001 | 3.29 +/− 0.18 (4) | NS$^b$ |
| Experiment 2 | | | | |
| huIgG control (killed D7) | 3.35 +/− 0.21 (3) | | 4.04 +/− 0.34 (3) | |
| mLTβR-Ig (D0, +3; 0.3, 0.2) ↓ | 2.37 +/− 0.24 (4) | 0.0024 | 3.04 +/− 0.19(4) | 0.004 |
| Experiment 3 | | | | |
| huIgG control (killed D6) | 2.34 +/− 0.11 (5) | | 2.93 +/− 0.57 (5) | |
| mLTβR-Ig (D-3: 0.4) | 1.10 +/− 0.38 (3) | 0.0024 | 2.27 +/− 1.39 (3) | NS |
| mLTβR-Ig (D-3, 0: 0.4, 0.3) ↑ | 0.78 +/− 0.02 (3) | <0.0001 | 3.95 +/− 0.53 (3) | 0.046 |
| mLTβR-Ig (D0: 0.3) | 0.92 +/− 0.10 (3) | <0.0001 | 3.25 +/− 0.15 (3) | NS |

$^a$Organ weight as percent of total body weight. Untreated LN weight is typically 0.5% of total body weight.
$^b$NS = not significant.
$^c$mLTBR-Ig is a fusion protein between mLTBR extracellular domain and the CH2 and CH3 region of hIgG1.

In other embodiments, it may be desirable to administer the inhibitors of the LT pathway simultaneously with, or prior or subsequent to, administration of radiation therapy. It will be apparent to those skilled in the art what the preferred therapy is based upon individual variables such as the patient's condition and the tumor being treated.

Inhibitory anti-LTβ-R Abs and other LT-β-R blocking agents can be identified using methods previously described in the art. (co-pending U.S. application Ser. No. 08/378,968).

The LTβ-R blocking agents in one embodiment of this invention comprise soluble LT-β receptor molecules. The sequence of the extracellular portion of the human LTβ-R, is known to encode the ligand binding domain (see FIG. 1). Using that sequence information in FIG. 1 and recombinant DNA techniques well known in the art, functional fragments encoding the LTβ-R ligand binding domain can be cloned into a vector and expressed in an appropriate host to produce a soluble LTβ-R molecule.

A soluble LT-β receptor comprising amino acid sequences selected from those shown in FIG. 1 may be attached to one or more heterologous protein domains ("fusion domain") to increase the in vivo stability of the receptor fusion protein, or to modulate its biological activity or localization.

Preferably, stable plasma proteins—which typically have a half-life greater than 20 hours in the circulation—are used to construct the receptor fusion proteins. Such plasma proteins include but are not limited to: immunoglobulins, serum albumin, lipoproteins, apolipoproteins and transferrin. Sequences that can target the soluble LTβ-R molecule to a particular cell or tissue type may also be attached to the LTβ-R ligand binding domain to create a specifically-localized soluble LTβ-R fusion protein.

All or a functional portion of the LTβ-R extracellular region (FIG. 1) comprising the LTβ-R ligand binding domain may be fused to an immunoglobulin constant region like the Fc domain of a human IgG1 heavy chain (Browning et al., *J. Immunol.*, 154, pp. 33-46 (1995)). Soluble receptor-IgG fusion proteins are preferable, and are common immunological reagents, and methods for their construction are known in the art (see e.g., U.S. Pat. No. 5,225,538 incorporated herein by reference).

A functional LTβ-R ligand binding domain may be fused to an immunoglobulin (Ig) Fc domain derived from an immunoglobulin class or subclass other than IgG1. The Fc domains of antibodies belonging to different Ig classes or subclasses can activate diverse secondary effector functions. Activation occurs when the Fc domain is bound by a cognate Fc receptor. Secondary effector functions include the ability to activate the complement system, to cross the placenta, and to bind various microbial proteins.

If it would be advantageous to harm or kill the LT ligand-bearing target cell, one could select an especially active Fc domain (IgG1) to make the LTβ-R-Fc fusion protein. Alternatively, if it would be desirable to target the LTβ-R-Fc fusion to a cell without triggering the complement system, an inactive IgG4 Fc domain could be selected.

Mutations in Fc domains that reduce or eliminate binding to Fc receptors and complement activation have been described (S. Morrison, *Annu. Rev. Immunol.*, 10, pp. 239-65 (1992)). These or other mutations can be used, alone or in combination, to optimize the activity of the Fc domain used to construct the LTβ-R-Fc fusion protein.

Different amino acid residues forming the junction point of the receptor-Ig fusion protein may alter the structure, stability and ultimate biological activity of the soluble LT-β receptor fusion protein. One or more amino acids may be added to the C-terminus of the selected LTβ-R fragment to modify the junction point with the selected fusion domain.

The N-terminus of the LT-βR fusion protein may also be varied by changing the position at which the selected LTβ-R DNA fragment is cleaved at its 5' end for insertion into the recombinant expression vector. The stability and activity of each LTβ-R fusion protein may be tested and optimized using routine experimentation and the assays for selecting LTβ-R blocking agents described herein.

Using the LTβ-R ligand binding domain sequences within the extracellular domain shown in FIG. 1, amino acid sequence variants may also be constructed to modify the affinity of the soluble LT-β receptor or fusion protein for LT ligand. The soluble LTβ-R molecules of this invention can compete for surface LT ligand binding with endogenous cell surface LT-β receptors. It is envisioned that any soluble molecule comprising a LTβ-R ligand binding domain that can compete with cell surface LT-β receptors for LT ligand binding is a LT-β-R blocking agent that falls within the scope of the present invention.

In another embodiment of this invention, antibodies directed against the human LT-β receptor (anti-LT-β-R Abs) function as LTβ-R blocking agents. The anti-LT-βR Abs of this invention can be polyclonal or monoclonal (mAbs) and can be modified to optimize their ability to block LTβ-R signaling, their in vivo bioavailability, stability, or other desired traits.

Polyclonal antibody sera directed against the human LT-β receptor are prepared using conventional techniques by injecting animals such as goats, rabbits, rats, hamsters or mice subcutaneously with a human LT-β receptor-Fc fusion protein (Example 1) in complete Freund's adjuvant, followed by booster intraperitoneal or subcutaneous injection in incomplete Freund's. Polyclonal antisera containing the desired antibodies directed against the LT-β receptor are screened by conventional immunological procedures.

Mouse monoclonal antibodies (mAbs) directed against a human LT-β receptor-Fc fusion protein are prepared as described in Example 5. A hybridoma cell line (BD.A8.AB9) which produces the mouse anti-human LT-β-R mAb BDA8 was deposited on Jan. 12, 1995 with the American Type Culture Collection (ATCC) (Rockville, Md.) according to the provisions of the Budapest Treaty, and was assigned the ATCC accession number HB11798. All restrictions on the availability to the public of the above ATCC deposits will be irrevocably removed upon the granting of a patent on this application.

Various forms of anti-LTβ-R antibodies can also be made using standard recombinant DNA techniques (Winter and Milstein, *Nature*, 349, pp. 293-99 (1991)). For example, "chimeric" antibodies can be constructed in which the antigen binding domain from an animal antibody is linked to a human constant domain (e.g. Cabilly et al., U.S. Pat. No. 4,816,567; Morrison et al., *Proc. Natl. Acad. Sci. U.S.A.*, 81, pp. 6851-55 (1984)). Chimeric antibodies reduce the observed immunogenic responses elicited by animal antibodies when used in human clinical treatments.

In addition, recombinant "humanized antibodies" which recognize the LT-β-R can be synthesized. Humanized antibodies are chimeras comprising mostly human IgG sequences into which the regions responsible for specific antigen-binding have been inserted (e.g. WO 94/04679). Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (inter-species) sequences in human antibodies, and are less likely to elicit immune responses in the treated subject.

Construction of different classes of recombinant anti-LT-β-R antibodies can also be accomplished by making chimeric or humanized antibodies comprising the anti-LT-β-R variable domains and human constant domains (CH1, CH2, CH3) isolated from different classes of immunoglobulins. For example, anti-LT-β-R IgM antibodies with increased antigen binding site valencies can be recombinantly produced by cloning the antigen binding site into vectors carrying the human T chain constant regions (Arulanandam et al., *J. Exp. Med.*, 177, pp. 1439-50 (1993); Lane et al., *Eur. J. Immunol.*, 22, pp. 2573-78 (1993); Traunecker et al., *Nature*, 339, pp. 68-70 (1989)).

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modeling (Queen et al., *Proc. Natl. Acad. Sci. U.S.A.*, 86, pp. 10029-33 (1989); WO 94/04679).

It may be desirable to increase or to decrease the affinity of anti-LTβ-R Abs for the LTβ-R depending on the targeted tissue type or the particular treatment schedule envisioned. For example, it may be advantageous to treat a patient with constant levels of anti-LTβ-R Abs with reduced ability to signal through the LT-β pathway for semi-prophylactic treatments. Likewise, inhibitory anti-LTβ-R Abs with increased affinity for the LTβ-R may be advantageous for short-term treatments.

Anti-LT-β-R Antibodies As LT-β-R Blocking Agents

Anti-LT-β-R antibodies that act as LTβ-R blocking agents may be selected by testing their ability to inhibit LTβ-R-induced cytotoxicity in tumor cells. By testing other antibodies directed against the human LTβ receptor, it is expected that additional anti-LT-β-R antibodies that function as LTβ-R blocking agents in humans can be identified using routine experimentation and the assays described herein.

Another preferred embodiment of this invention involves compositions and methods which comprise antibodies directed against LT ligand that function as LT-β-R blocking agents. As described above for the anti-LTβ-R Abs, anti-LT ligand antibodies that function as LTβ-R blocking agents can be polyclonal or monoclonal, and can be modified according to routine procedures to modulate their antigen binding properties and their immunogenicity.

The anti-LT antibodies of this invention can be raised against either one of the two LT subunits individually, including soluble, mutant, altered and chimeric forms of the LT subunit. If LT subunits are used as the antigen, preferably they are LT-β subunits. If LT-α subunits are used, it is preferred that the resulting anti-LT-α antibodies bind to surface LT ligand and do not cross-react with secreted LT-α or modulate TNF-R activity.

Alternatively, antibodies directed against a homomeric (LT-β) or a heteromeric (LT-α/β) complex comprising one or more LT subunits can be raised and screened for activity as LT-β-R blocking agents. Preferably, LT-α1/β2 complexes are used as the antigen. As discussed above, it is preferred that the resulting anti-LT-α 1/β2 antibodies bind to surface LT ligand without binding to secreted LT-α and without affecting TNF-R activity.

The production of polyclonal anti-human LT-α antibodies is described in applicants' co-pending application (WO 94/13808). Monoclonal anti-LT-α and anti-LT-β antibodies have also been described (Browning et al., *J. Immunol.*, 154, pp. 33-46 (1995)).

Compounds

Therapeutic compounds useful for the methods of the invention include any compound that blocks the interaction of LT-β with LT-β-receptor and therefore inhibits the LT pathway. Anti-LT compounds specifically contemplated include polyclonal antibodies and monoclonal antibodies (mAbs), as well as antibody derivatives such as chimeric molecules, humanized molecules, molecules with reduced effector functions, bispecific molecules, and conjugates of antibodies.).

The invention also includes anti-LT-β and anti-LT-β receptor molecules of other types, such as complete Fab fragments, F(ab')$_2$ compounds, V$_H$ regions, F$_V$ regions, single chain antibodies (see, e.g., WO 96/23071), polypeptides, fusion constructs of polypeptides, fusions of LT-β receptor, and small molecule compounds such as small semi-peptidic compounds or non-peptide compounds, all capable of blocking the LT pathway.

Various forms of antibodies may also be produced using standard recombinant DNA techniques (Winter and Milstein, Nature 349: 293-99, 1991). For example, "chimeric" antibodies may be constructed, in which the antigen binding domain from an animal antibody is linked to a human constant domain (an antibody derived initially from a nonhuman mammal in which recombinant DNA technology has been used to replace all or part of the hinge and constant regions of the heavy chain and/or the constant region of the light chain, with corresponding regions from a human immunoglobin light chain or heavy chain) (see, e.g., Cabilly et al., U.S. Pat. No. 4,816,567; Morrison et al., Proc. Natl. Acad. Sci. 81: 6851-55, 1984). Chimeric antibodies reduce the immunogenic responses elicited by animal antibodies when used in human clinical treatments.

In addition, recombinant "humanized" antibodies may be synthesized. Humanized antibodies are antibodies initially derived from a nonhuman mammal in which recombinant DNA technology has been used to substitute some or all of the amino acids not required for antigen binding with amino acids from corresponding regions of a human immunoglobin light or heavy chain (chimeras comprising mostly human IgG sequences into which the regions responsible for specific antigen-binding have been inserted)(see, e.g., PCT patent application WO 94/04679). Animals are immunized with the desired antigen, the corresponding antibodies are isolated and the portion of the variable region sequences responsible for specific antigen binding are removed. The animal-derived antigen binding regions are then cloned into the appropriate position of the human antibody genes in which the antigen binding regions have been deleted. Humanized antibodies minimize the use of heterologous (inter-species) sequences in human antibodies and are less likely to elicit immune responses in the treated subject.

Also useful in the methods and compositions of this invention are primate or primatized antibodies.

Antibody fragments and univalent antibodies may also be used in the methods and compositions of this invention. Univalent antibodies comprise a heavy chain/light chain dimer bound to the Fc (or stem) region of a second heavy chain. Fab regions refers to those portions of the chains which are roughly equivalent, or analogous, to the sequences which comprise the Y branch portions of the heavy chain and to the light chain in its entirety, and which collectively (in aggregates) have been shown to exhibit antibody activity. A Fab protein includes aggregates of one heavy and one light chain (commonly known as Fab'), as well as tetramers which correspond to the two branch segments of the antibody Y, (commonly known as F(ab)$_2$), whether any of the above are covalently or non-covalently aggregated, so long as the aggregation is capable of selectively reacting with a particular antigen or antigen family.

In addition, standard recombinant DNA techniques can be used to alter the binding affinities of recombinant antibodies with their antigens by altering amino acid residues in the vicinity of the antigen binding sites.

Subjects

The subjects for whom the methods of the invention are intended have follicular lymphomas.

Routes of Administration

The compounds of the invention may be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the invention, by such means as depot injections. Some forms of LT blocking compounds may be suitable for oral administration, and could be formulated as suspensions or pills.

Dosages and Frequency of Treatment

The amount of and frequency of dosing for any particular compound to be administered to a patient for a given immune complex disease is a judgment made by the patient's physician, based on a number of factors. The general dosage is established by preclinical and clinical trials, which involve extensive experiments to determine the beneficial and deleterious effects on the patient of different dosages of the compound. Even after such recommendations are made, the physician will often vary these dosages for different patients based on a variety of considerations, such as a patient's age, medical status, weight, sex, and concurrent treatment with other pharmaceuticals. Determining the optimal dosage for each LT blocking compound used to treat follicular lymphoma is a routine matter for those of skill in the pharmaceutical and medical arts.

Generally, the frequency of dosing would be determined by the attending physician, and might be either as a single dose, or repeated daily, at intervals of 2-6 days, weekly, biweekly, or monthly.

Combination therapies according to this invention for treatment of follicular lymphomas together with other agents targeted at such lymphomas, including, for example, radiation, chemotherapy, or other therapies known to those skilled in the art.

An LT blocking compound of the invention is administered to a patient in a pharmaceutically acceptable composition, which may include a pharmaceutically-acceptable carrier. Such a carrier is relatively non-toxic and innocuous to a patient at concentrations consistent with effective activity of the blocking compound or other active ingredients, so that any side effects ascribable to the carrier do not vitiate the beneficial effects of the active ingredients of the composition. The composition may include other compatible substances; compatible, as used herein, means that the components of the pharmaceutical composition are capable of being commingled with the LT blocking compound, and with each other, in a manner such that there is no interaction which would substantially reduce the therapeutic efficacy of the pharmaceutical. Formulations of the present invention suitable for oral administration may be presented as discrete units such as capsules, cachets, tablets, pills or lozenges, each containing a predetermined amount of the potentiating compound as a powder or granules; as liposomes; or as a suspension in an aqueous liquor or non-aqueous liquid such as a syrup, an elixir, an emulsion or a draught.

The compositions of the invention may be provided in containers suitable for maintaining sterility, protecting the activity of the active ingredients during proper distribution and storage, and providing convenient and effective accessibility of the composition for administration to a patient. For an injectable formulation of a LT blocking compound, the composition might be supplied in a stoppered vial suitable for withdrawal of the contents using a needle and syringe. The vial would be intended for either single use or multiple uses. The composition might also be supplied as a prefilled syringe. In some instances, the contents would be supplied in liquid formulation, while in others they would be supplied in a dry or lyophilized state, which would require reconstitution with a standard or a supplied diluent to a liquid state. Where the compound is supplied as a liquid for intravenous administration, it might be provided in a sterile bag or container suitable for connection to an intravenous administration line or catheter. In instances where the blocking compound is orally administered in tablet or pill form, the compound might be supplied in a bottle with a removable cover. The containers may be labeled with information such as the type of compound, the name of the manufacturer or distributor, the indication, the suggested dosage, instructions for proper storage, or instructions for administration.

REFERENCES

1. Tsiagbe, V. K., Inghirami, G. & Thorbecke, G. J. The physiology of germinal centers. *Crit Rev Immunol* 16, 381-421 (1996).
2. Freedman, A. S. & Nadler, L. M. in *Cancer Medicine* 3rd Ed. (ed. Holland, J. F. e.a.) 2028-2068 (Lea&Febiger, London, 1994).
3. Lasky, J. L., Ponzio, N. M. & Thorbecke, G. J. Characterization and growth factor requirements of SJL lymphomas. I. Development of a B cell growth factor-dependent in vitro cell line, cRCS-X [published erratum appears in J Immunol 1988 Apr. 1; 140(7):2478]. *J Immunol* 140, 679-87 (1988).
4. Lasky, J. L. & Thorbecke, G. J. Characterization and growth factor requirements of SJL lymphomas. H. Interleukin 5 dependence of the in vitro cell line, cRCS-X, and influence of other cytokines. *Eur J Immunol* 19, 365-71 (1989).
5. Ponzio, N. M., Brown, P. H. & Thorbecke, G. J. Host-tumor Interactions in the SJL lymphoma model. *Intern. Rev. immunol.* 1, 273-301 (1986).
6. Tsiagbe, V. K., et al. Syngeneic response to SJL follicular center B cell lymphoma (reticular cell sarcoma) cells is primarily in V beta 16+CD4+ T cells. *J Immunol* 150, 5519-28 (1993).
7. Matsumoto, M., et al. Distinct roles of lymphotoxin alpha and the type I tumor necrosis factor (TNF) receptor in the establishment of follicular dendritic cells from non-bone marrow-derived cells. *J Exp Med* 186, 1997-2004 (1997).
8. Mackay, F., Majeau, G. R., Lawton, P., Hochman, P. S. & Browning, J. L. Lymphotoxin but not tumor necrosis factor functions to maintain splenic architecture and humoral responsiveness in adult mice. *Eur J Immunol* 27, 2033-42 (1997).
9. Katz, I. R., Chapman-Alexander, J., Jacobson, E. B., Lerman, S. P. & Thorbecke, G. J. Growth of SJL/J derived transplantable reticulum cell sarcoma as related to its ability to induce T-cell proliferation in the host. III. Studies on thymectomized and congenitally athymic SJL mice. *Cellular Immunol.* 65, 84-92 (1981).

What is claimed is:

1. A method for altering the survival or maintenance of a follicular dendritic cell in a subject having a B cell lymphoma comprising administering an amount of a composition comprising a soluble lyraphotoxin-beta receptor (LT-beta-R) and a pharmaceutically acceptable carrier, such that the survival or maintenance of a follicular dendritic cell is altered, and further comprising administering either radiation or at least one chemotherapeutic agent to the subject.

2. The method of claim 1, wherein altering the survival or maintenance of a follicular dendritic cell comprises inhibiting the survival of the follicular dendritic cell.

3. The method of claim 1, wherein altering the survival or maintenance of a follicular dendritic cell comprises disrupting the function of a mature follicular dendritic cell.

4. The method of claim 1, wherein altering the survival or maintenance of a follicular dendritic cell comprises disrupting germinal center function.

5. The method of claim 1, wherein the subject is a mammal.

6. A method for altering the survival or maintenance of a follicular dendritic cell in a human subject having a B cell lymphoma, the method comprising administering to the subject a pharmaceutical composition comprising a polypeptide that comprises a salable, ligand-binding domain of human lymphotoxin-beta receptor (LT-beta-R) fused to a human IgG1 Fc domain, such that the survival or maintenance of a follicular dendritic cell in a human subject is altered.

7. The method of claim 1, further comprising administering to said subject a bone marrow transplant.

8. The method of claim 1, wherein the composition comprises a soluble LT-beta-R fused to one or more heterologous protein domains.

9. The method of claim 8, wherein the heterologous protein domain is selected from the group consisting of an immunoglobulin, a serum albumin, a lipoprotein, an apolipoprotein, and a transferrin.

10. The method of claim 8, wherein the heterologous protein domain is a human immunoglobulin Fc domain.

11. The method of claim 1, wherein the soluble LT-beta-R comprises a ligand binding domain that can selectively bind to a surface LT ligand.

12. The method of claim 1, wherein the soluble LT-beta-R comprises an extracellular domain of LT-beta-R.

13. The method of claim 1, wherein the soluble LT-beta-R is human LT-beta-R.

14. The method of claim 13, wherein the soluble LT-beta-R further comprises a human immunoglobulin Fc domain.

15. The method of claim 14, wherein the human immunoglobulin Fc domain is IgG1.

16. The method of claim 1, wherein the soluble LT-beta-R comprises SEQ ID NO:1, or a functional fragment thereof.

17. The method of claim 5 or 6, wherein the subject is a human.

18. The method of claim 6, wherein the soluble, ligand-binding domain of human LT-beta-R comprises the sequence of SEQ ID NO:1, or a functional fragment thereof.

19. A method for altering the survival and maintenance of follicular dendritic cells in a subject having a B cell lymphoma comprising administering an inhibitor of the interaction between LT-beta and its receptor and further comprising administering either radiation or at least one chemotherapeutic agent to the subject.

20. The method of claim 19, wherein the inhibitor comprises a soluble lymphotoxin-beta receptor (LT-beta-R).

* * * * *